US006626665B1

(12) United States Patent
Keles

(10) Patent No.: US 6,626,665 B1
(45) Date of Patent: Sep. 30, 2003

(54) DEVELOPED MAXILLARY MOLAR DISTALIZATION APPLIANCE

(76) Inventor: Ahmet Ozlem Keles, Halaskargazi Cad. Hala Apt. 275/4, Istanbul, Osmanbey (TR), 80220

( * ) Notice: Subject to any disclaimer, the term of this patent is extended or adjusted under 35 U.S.C. 154(b) by 0 days.

(21) Appl. No.: 09/890,395

(22) PCT Filed: Nov. 30, 1999

(86) PCT No.: PCT/TR99/00052

§ 371 (c)(1),
(2), (4) Date: Oct. 1, 2001

(87) PCT Pub. No.: WO01/39687

PCT Pub. Date: Jun. 7, 2001

(51) Int. Cl.$^7$ ................................................. A61C 3/00
(52) U.S. Cl. ............................................. 433/18; 433/7
(58) Field of Search ................................ 433/7, 18, 24

(56) References Cited

U.S. PATENT DOCUMENTS

| 1,582,570 A | * | 4/1926 | Brust ............................. 433/7 |
| 3,162,948 A | * | 12/1964 | Gerber ........................... 433/7 |
| 5,002,485 A | | 3/1991 | Aagesen |
| 5,064,370 A | | 11/1991 | Jones |
| 5,785,520 A | * | 7/1998 | Carano et al. .................. 433/7 |
| 5,829,970 A | * | 11/1998 | Yousefian ....................... 433/7 |

OTHER PUBLICATIONS

Keles, Ahmet Ozlem, "Maxillary unilateral molar distalization with slidng mechanics: a preliminary investigation" European Journal of Orthodontics No. 23, 2001, pp 507–515.
Keles, Ahmet Ozlem, "Bilateral Maxillary Molar Distalization with Sliding Mechanics: Keles Slider" World Journal of Orthodontics, vol. 3, No. 1, 2002 pp. 1–10.

\* cited by examiner

*Primary Examiner*—Nicholas D. Lucchesi
(74) *Attorney, Agent, or Firm*—Harrison & Egbert

(57) ABSTRACT

For maxillary molar distalization a newly developed maxillary molar distalization appliance is introduced. Maxillary first molars and first premolars were banded. On the palatal side of the Class II first molar bands 0.45 inch diameter tubes were soldered. First premolar band were attached with 1.1 mm in diameter s.s. retaining wires to a wide acrylic Nance button. The acrylic button also included an anterior bit plane. The purpose of creating an anterior bit plane was to disocclude the posterior teeth, enhance the molar distalization and correct the anterior deep bit. On the palatal side of molars 0.9 mm in diameter s.s. wires were embedded into the acrylic about 5 mm apical to the gingival margin of the first molars, which passed through the tube and oriented parallel to the occlusal plane. This force system would allow applying consistent force at the level of center of resistance of the first molars.

8 Claims, 3 Drawing Sheets

DEVELOPED MAXILLARY MOLAR DISTALIZATION APPLIANCE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

This invention is related to an orthdontic appliance, which moves the maxillary molars back and corrects their positions.

BACKGROUND OF THE INVENTION

Over the past ten years non-extraction treatment and non-compliance therapies have become more popular in correction of Class II malocclusions. Treatment of Class II cases usually requires distal movement of maxillary molars in order to achieve Class I molar and canine relationship. However, if the maxillary molars are not distalized bodily and adequate anchorage is not established to move premolars and canines distally, anchorage will be lost very easily. In the literature, various types of devices were developed for molar distalization. For years headgear was used routinely for distal movement of maxillary molars. However, headgear totally relied on patient cooperation, which could reduce treatment success and increase treatment duration. On the other hand, headgear was rejected by many patients because of aesthetic and social concern.

The difficulties of headgear wear and dependence on patient cooperation stimulated many investigators to develop new intra-oral devices and techniques for distal movement of molars. In 1978 Blechman, in 1988 Gianelly, in 1992 Bondemark used magnets for molar distalization. In 1991, Gianelly and in 1994 Bondemark used super-elastic Ni-Ti coil springs for distal movement of maxillary molars.

In 1992 Hilgers developed the pendulum appliance for distal movement of molar. The application consisted of TMA springs and a button on the palate. The appliance got its popularity in the mid nineties. In 1996 Ghosh and nanda, in 1997 Byloff and Darendeliler and in 2000 Bussck and McNamara and another study in the same Year, Joseph and Butchart, conducted studies on the pendulum appliance. From the distalization point of view all of the pendulum studines demonstrated that the molar were distalized with the expense of distal tipping. The amount of tippin in all of these pendulum studies varied from 6.07 to 17.7

Keles and Sayinsu in 2000 developed IBMD for molar distalization. Their distalizing (0.032"×0.032") TMA spring design was composed of two components which enabled moving the molars bodily. Their results showed that the molars distalized without tipping; however, the expense of bodily distalization was significant anchorage loss.

In conclusion all the newly introduced intraoral distalization appliance which were developed in the last decade of the 20$^{th}$ century eliminated the patient cooperation; such that, distal tipping of molar and anchorage loss are the main concerns of investigators and the orthodontists.

BRIEF SUMMARY OF THE INVENTION

For maxillary molar distalization, a newly developed intraoral appliance was used. Keles Slider was composed of two premolar and two molar bands and the anchorage unit was composed of a wide Nance button. On the palatal side, the point of distal force application was carried towards the center of resistance of the maxillary 1$^{st}$ molar in order to achieve bodily distal movement. Ni-Ti coil springs were used and 200 g of distal force was applied to the Class II 1$^{st}$ molars.

DETAILED DESCRIPTION OF THE INVENTION

Figure 1:
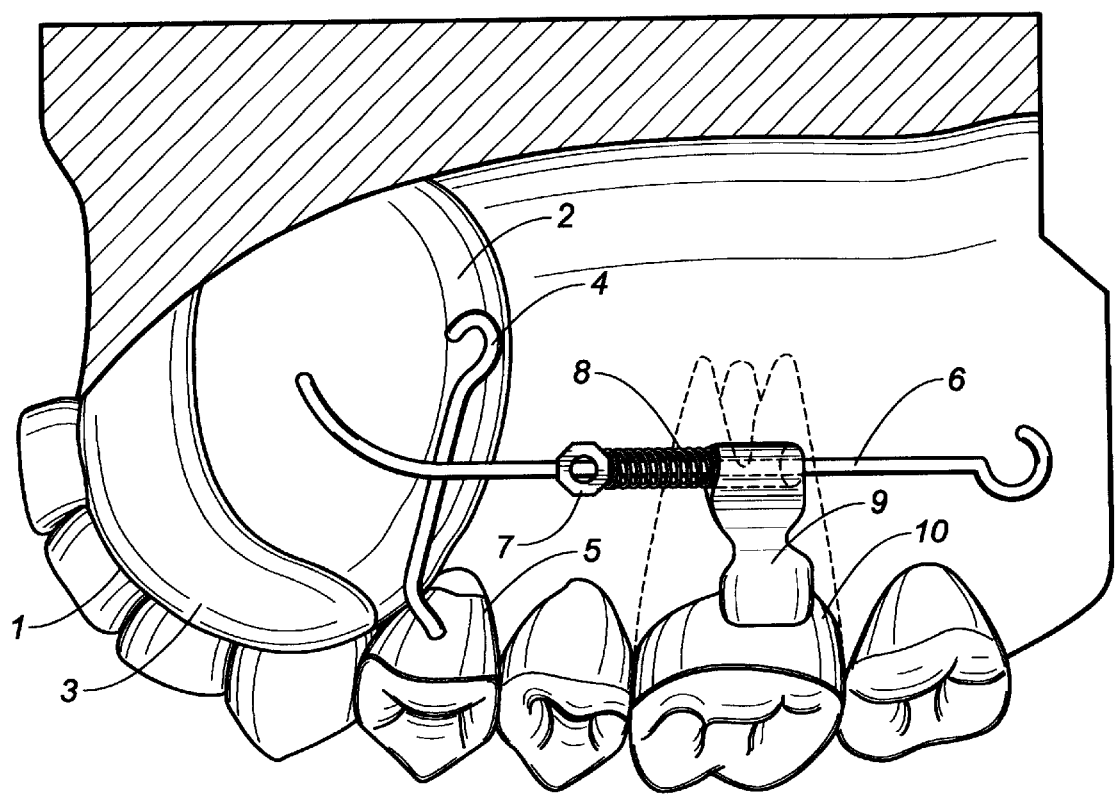
FIG. 1 is an inner side plan view, or lateral palatal view, which shows the present invention as attached to a mouth of a patient.
Figure 2:
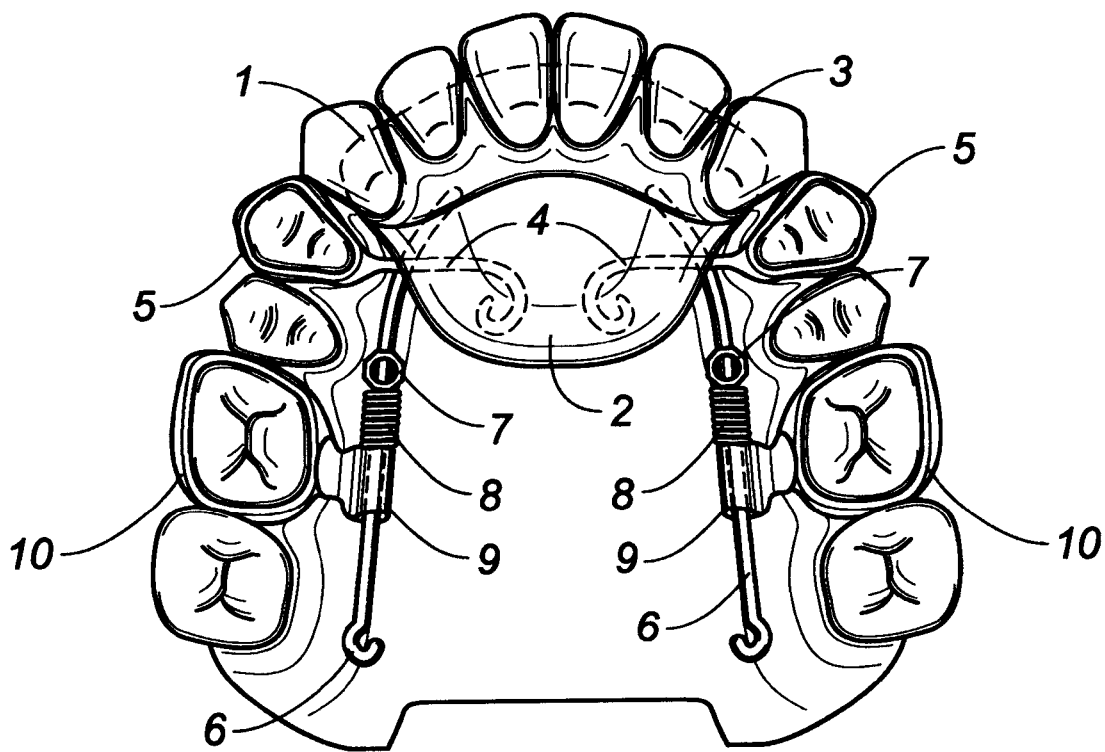
FIG. 2 is a top view, or occlusal view, which shows the present invention as attached to a mouth of a patient.
Figure 3:
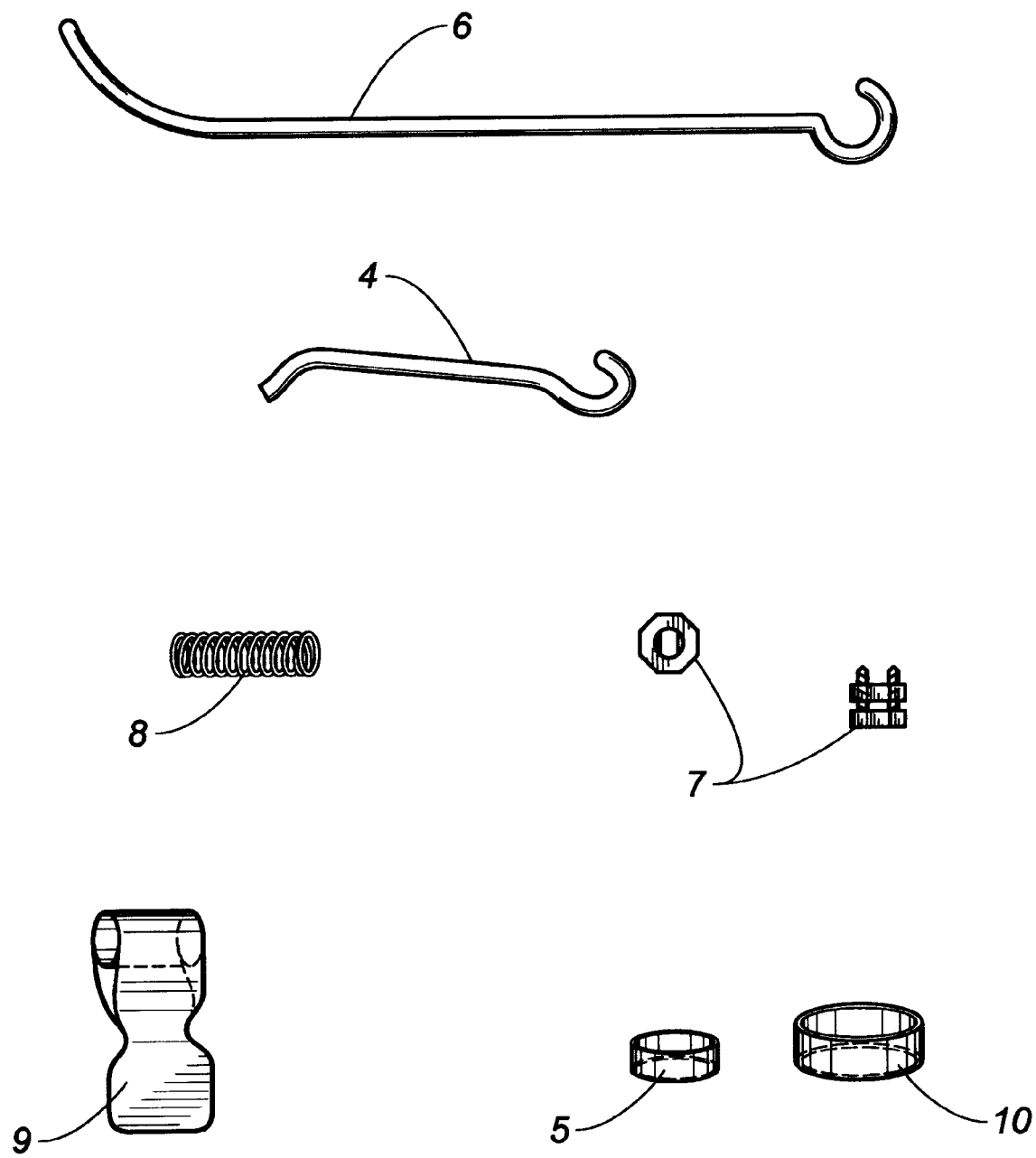
FIG. 3 is an exploded plan view of seven parts of the present invention.

The framework (1) of the appliance consists of various components. Maxillary first molars (10) and first premolars (5) were banded. On the palatal side of the Class II first molar bands 0.045 inch diameter tubes (9) were soldered (Leone A 076-45). First premolar bands were attached with 1.1 mm in diameter s.s. retaining wires (4) to a wide acrylic Nance button (2). The acrylic button also consisted of an anterior bite plane (3). The purpose of creating an anterior bite plane was to disocclude the posterior teeth, enhance the molar distalization and correct the anterior deep bite. On the palatal side of molars 0.9 mm in diameter s.s. wires (6) were embedded into the acrylic about 5 mm apical to the gingival margin of the first molars, which passed through the tube (9) and oriented parallel to the occlusal plane. (See FIG. 2) For molar distalization 2 cm in length, 0.9 mm in diameter Ni-Ti coil spring (8) was placed in between the lock on the wire and tube in full compression. The amount of force generated with the full compression of the 2 cm open coil was about 200 gr. This force system would allow applying consistent force at the level of center of resistance of the first molars. Biomechanics of the force system was presented at FIG. 1. Patients were seen once every month and the Gurin lock (7) (3M Unitek, USA, 560-400) was activated with the Gurin lock wrench (3M Unitek, USA, 810-002).

I claim:

1. An orthodontic appliance which pushes molars of an upper jaw of a user back to correct an abnormal position of the user's teeth, the appliance comprising a supporting acrylic plate comprised of a frontal flat bite palate and a dental support means receiving support from eight upper front teeth of the user of the appliance and soft tissue and bony support from palatal gingiva and underlining bone of an upper jaw of the user;

first premolar bands and first molar bands located on both sides of the user's mouth, each of said bands securable around respective first premolar and first molar teeth of the user on both sides of the user's mouth, wherein said first premolar bands are connected to the supporting acrylic plate with rigid wires so as to anchor the appliance;

tubes being soldered from extension parts thereof to the first molar bands on a palatal side of the user's mouth, wherein openings of the tubes are oriented towards gingiva of the user's mouth at a higher level;

a rigid wire rod being passed across the tubes freely, wherein a distal end is comprised of a helix and a mesial end is embedded in the supporting acrylic plate;

a lock being placed on a wire between the supporting acrylic plate and the tubes; and a compression spring being placed on the wire rod which is located between the lock and the tubes.

2. An appliance according to claim 1, further comprising a supporting acrylic framework comprised of dental support means receiving support from eight upper front teeth of the user of the appliance and soft tissue and bony support from the palatal gingiva and the underlining bone of the upper jaw of the user's mouth.

3. An appliance according to claim 2, wherein the acrylic supporting framework is further comprised of an anterior bite plane to open a bite anteriorly and also to stop upper and lower posterior teeth of the user from touching.

4. An appliance according to claim 2, wherein the supporting framework is comprised of a dental support means receiving support from eight upper front teeth of the user, and dental support means receiving support from a palatal side of six upper anterior teeth of the user and the first premolars of the user on both sides of the mouth of the user which were banded and connected with wires to the framework.

5. An appliance according to claim 1, wherein the tubes are soldered to the first molar bands on the palatal side of the user, wherein a tube means, is comprised of stainless steel and has an extension for soldering, wherein said extension is soldered to the molar band and the opening of the tube is located more towards a gingival side of the user's mouth, a tubular axis of said tube being oriented parallel to the occlusal surface of the molars of the user, and wherein said tube slides freely along the rigid wire without any friction.

6. An appliance according to claim 1, wherein a rigid wire rod comprises a heavy stainless steel wire which passes across the tubes freely with a distal end comprised of a helix stop and the mesial end embedded in acrylic and connected to the supporting acrylic plate.

7. An appliance according to claim 1, wherein a lock is placed on a wire to compress the coil spring between the supporting acrylic plate and a tube means, the lock being able to be tightened and loosened with a wrench which allows compressing the coil spring on the wire against the tube means and wherein, by pushing towards distally and tightening the lock on the wire and compressing the coil spring, force will be generated and the tube means tends to move distally which is soldered to the molar band and wherein distal movement of the tube means would push the molars back by receiving anchorage from the supporting framework.

8. An appliance according to claim 1, wherein a compression spring is placed on a wire rod which is located between the lock and the tube means, wherein the compression spring is the active component of the appliance which applies force to the first molars at a higher level closer to the center of resistance of the molars.

* * * * *